USOO5897589A

United States Patent [19]
Cottenceau et al.

[11] Patent Number: 5,897,589
[45] Date of Patent: Apr. 27, 1999

[54] ENDOLUMINAL MEDICAL IMPLANT

[75] Inventors: Jean-Philippe Cottenceau, Antony; Gérard Chevillon, Montrouge; Guy Nadal; Maurice Roussigne, both of Poitiers, all of France

[73] Assignee: B.Braun Celsa, France

[21] Appl. No.: 08/890,557

[22] Filed: Jul. 9, 1997

[30] Foreign Application Priority Data

Jul. 10, 1996 [FR] France ................................ 96 08610

[51] Int. Cl.⁶ ................................ A61F 2/06; A61F 2/04
[52] U.S. Cl. ................................................ 623/1; 623/12
[58] Field of Search .................... 623/1, 12; 606/192, 606/194, 195, 198

[56] References Cited

U.S. PATENT DOCUMENTS

| 5,275,622 | 1/1994 | Lazarus et al. | 623/1 |
| 5,405,377 | 4/1995 | Cragg . | |
| 5,421,955 | 6/1995 | Lau et al. . | |
| 5,693,088 | 12/1997 | Lazarus | 623/1 |

FOREIGN PATENT DOCUMENTS

| 0539237 | 4/1993 | European Pat. Off. . |
| 0539273 | 4/1993 | European Pat. Off. . |
| 0540290 | 5/1993 | European Pat. Off. . |
| 0686379 | 12/1995 | European Pat. Off. . |
| 2722678 | 1/1996 | France . |
| WO9417754 | 8/1994 | WIPO . |
| WO9521592 | 8/1995 | WIPO . |
| WO9526695 | 10/1995 | WIPO . |

*Primary Examiner*—Mickey Yu
*Assistant Examiner*—John M. Black
*Attorney, Agent, or Firm*—Rothwell, Figg, Ernst & Kurz, P.C.

[57] ABSTRACT

An endoluminal medical prosthesis has a frame, a flexible sleeve, and means for fastening the flexible sleeve to the frame. The frame includes a plurality of adjacent, axially-spaced undulating or meandering tubular structures, the undulations or meanders being formed by elongate segments arranged in V- or U-formation, with apices therebetween. The flexible sleeve is substantially coaxial with the frame and channels a fluid flowing in the duct. The attaching element, which includes a flexible thread, wraps around and extends from an elongate segment of one meandering structure of the frame to an elongate segment of an adjacent, axially spaced meandering structure of the frame, preferably passing through the flexible sleeve with each wrap or turn around a segment.

9 Claims, 5 Drawing Sheets

5,897,589

ENDOLUMINAL MEDICAL IMPLANT

FIELD OF THE INVENTION

The invention relates to endoluminal medical prosthesesl.

DESCRIPTION OF BACKGROUND ART

Endoluminal medical prostheses are devices placed inside a duct of a living body for the treatment of certain vascular deformations such as aneurism. They often are implanted by an endoluminal route, but in other cases may be implanted via vessel stripping. When implanted endoluminally, the prosthesis may be implanted using a balloon which i inflated in the implantation duct, thereby causing the stent to be dilated plastically in order to press against the walls of the duct.

Various vascular prostheses are known in the prior art. A vascular prosthesis may comprise a frame, a flexible sleeve, and attaching or connecting mean between the sleeve and the frame. The frame is defined by one or more tubular sections arranged along at least one axis, with the sections comprising a relatively rigid meandering or undulating structure. The meandering structures of the tubular sections are coiled or wound in one or more coiling levels and have apices between which elongate segments extend.

FIGS. 1–6 illustrate the construction of the frames of various prior art protheses. FIG. 1 shows a prior art prosthesis having a frame 1 comprising a plurality of meandering or undulating structures 3, 5, 7, and 9. The meandering structures 3, 5, 7, and 9 may be made from a relatively rigid material such as a stainless steel or Nitinol® wire.

The prior art device of FIG. 1 may be constructed as illustrated in FIG. 2. The meandering structures 3, 5, 7, and 9 are formed with substantially V-shaped undulation or meanders having rounded apices 11, and after every four peaks, for example, there is a rectilinear segment 12 that is substantially twice the length of the rectilinear segments 14 which form the meanders or undulations. The wires 3, 5, 7, and 9 are juxtaposedly offset along a series of directrix lines that are oriented substantially perpendicularly to the axis 21 of the completed frame 1. The meandering structures 3, 5, 7, and 9 are welded together in pairs at points 23 (depicted as short, slanted lines across the wires 3, 5, 7, and 9 in FIG. 2) where two adjacent meandering structures lie side-by-side.

After thus producing a flat structure, the structure is coiled or wound on itself to form a tubular structure, and the segments of meandering (such as those marked 25a and 25b for level 13) located at the end of each wire 3, 5, 7, or 9 are welded to each other. There is thus obtained the stepped structure shown in FIG. 1, which is composed of the four tubular sections 13, 15, 17, and 19 connected together by the double length segments 12.

The prior art prosthesis in FIG. 3 is a bifurcated prosthesis 10 comprising a principle section 27 to which two secondary branches or sections 29 and 31 are connected. The prior art device of FIG. 3 may be constructed as shown in FIG. 4, with the manufacture being nearly identical to that of the non-bifurcated device as illustrated in FIG. 2. The difference between the manufacture of the two can be seen at regions 33, where two substantially rectilinear segments of the structural wires 3, 5, 7, and 9 are not welded together, although they are still arranged side-by-side. It is the lack of intimate connection between the wires 5 and 7 at the levels marked 17a and 19a that allows one to form the two secondary branches 29 and 31 extending from the bifurcation zone 35.

FIG. 5 shows a monotube prosthesis constructed in accordance with U.S. Pat. No. 5,405,377, which is incorporated herein by reference. This prosthesis is formed from a single structural wire which is relatively rigid and resilient. The wire may be made from metal such as stainless steel, tental, or titanium, or it may be made from plastic having sufficient rigidity and resiliency to be twisted and subsequently coiled. The wire is twisted and subsequently coiled to form a continuous helix comprised of a series of loops connected at their apices to one another by small rings 41. The rings 41 connect all of the adjacent apices, e.g., 38a and 38b, of the zigzags formed by the wire 38.

Another prior art prosthesis is illustrated in FIG. 6. This prosthesis is disclosed in EP-A-540 290, which is incorporated herein by reference. The frame of the prosthesis, which consists of a tubular stent of constant circular cross-section, is a one piece unit produced from a thin metal plate by chemical erosion. It is thus possible to form a structure 43 having a series of windings at adjacent levels connected together, such as 47 and 49 or 49 and 51, by bridges of material 53 oriented parallel to the axis 55 of the completed frame 1.

The flexible sleeve of the prosthesis, which is substantially coaxial with the frame, channels a fluid which circulates in the duct of the body. The attaching means comprises at least one flexible thread which attaches the flexible sleeve to the frame. The flexible thread is not as rigid as the segments of the meandering structure and is arranged in such a manner that it wraps around at least one segment and passes through the sleeve to ensure the attachment.

One example of prostheses of this type is shown in EP-A-686 379. Other examples may be found, for example, in EP-A-540 290, WO-A-95/26 695, and WO-A-94/17754, each of which discloses a frame having several substantially coaxial coiling levels. The coiling levels are formed individually by a relatively rigid structure having meanders which include elongate segments, with the various levels being staggered and connected to one another successively, in pairs, by at least one of the structural segments.

In WO-A-95/21 592 and FR-A-2 707 434, the frame is constructed so as to form a bifurcated prosthesis. The frame comprises a principal tubular section and two secondary tubular sections connected to the principal tubular section at a substantially Y-shaped connection zone.

In prior art prostheses having fluid duct sleeves, such as those disclosed in EP-A-539 273 and in WO-A-95/26 695, certain deficiencies relating to the attachment of the sleeve to the frame have been noted. In EP-A-539 237, for example, the sleeve is attached to the frame by suture threads, made from nonbiodegradable material, which pass through the sleeve and are knotted around a structural segment of the frame to form small individual sutures. This is, however, only a punctuate connection, which is fairly time-consuming to produce, and the distance between two individual sutures has proven in practice to be fairly great. This distance may prove detrimental, especially if a suture becomes undone or torn, thus allowing the sleeve to "float" relative to the frame.

SUMMARY OF THE INVENTION

The invention provides a prosthesis in which the attachment of the sleeve to the frame is more secure and will not allow the sleeve to float, regardless of whether the sleeve is inside or outside the frame. To accomplish optimal securing of the sleeve to the frame, a prosthesis according to the invention has a frame with several tubular sections and/or several winding levels, and a flexible thread extends successively along at least two structural segments belonging to two of the several winding levels and/or to two of the staggered tubular sections.

With a prosthesis according to the invention, the speed of producing the assembly is improved, particularly when using a "straight stitch" with a helical coiling of the threads. Also, the "intimacy" of the contact between the sleeve and the structure is increased.

Furthermore, the invention implicitly solves a troublesome problem encountered with prior art prostheses, that problem being the apices of the meanders of the structure projecting or poking outward when the structure is curved, e.g., when implanted in a duct. To that extent, it is preferred for the flexible thread to pass, in going from one segment to the next, near or about the apices of the segments so as to restrain the apices when the prosthesis is curved.

According to other features of the invention, it is advantageous for the flexible thread to be wound about the segments substantially in a helix, i.e., in the manner of a substantially straight stitch. The segments should be arranged as continuations of one another, in a substantially rectilinear or helical direction, with the flexible thread extending in the same direction. For efficient positioning of the flexible sutures, the threads forming the sutures preferably pass from one level of the structure to the next without returning to a given level.

Further, to limit the risk of the thread running freely in case it breaks or tears, the flexible thread should be knotted at least once along its length and preferably several times at various places. According to a complementary feature, the thread preferably passes through the sleeve each time it wraps around a structural segment. It should likewise be noted that at least some of the flexible attachment threads preferably extend over at least the majority of the length of the prosthesis, this length being the length between the free axial ends of the prosthesis.

BRIEF DESCRIPTION OF THE DRAWINGS

A more detailed description of the invention will now be given with reference to the accompanying drawings, in which.

DETAILED DESCRIPTION OF THE PREFERRED EMBODIMENTS

Figure 7:
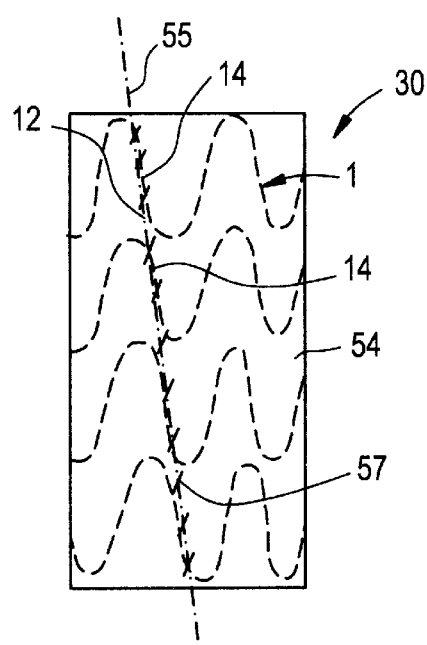
FIG. 7 shows the structure in FIG. 1, but with the addition of the flexible retaining threads which are characteristic of the invention.

FIG. 7 shows an embodiment of an endoluminal medical prosthesis according to the present invention. The prosthesis includes a frame 1, a flexible sleeve 54, and a flexible thread 57. The flexible sleeve 54 may be made of any suitable material such as nylon® or dacron® having a flexibility comparable to that of thin fabric. The thread 57 may be made of any suitable biocompatible natural or synthetic fiber which is more flexible than the meandering structures 3, 5, 7, 9, 38, 43, etc. forming the frame 1. One example is a nylon® material. In practice, any thread adapted to be used as a surgical suture is suitable. Optionally, a very fine metallic thread approximately 0.02 mm to 0.04 mm in diameter may also be used.

Figure 8:
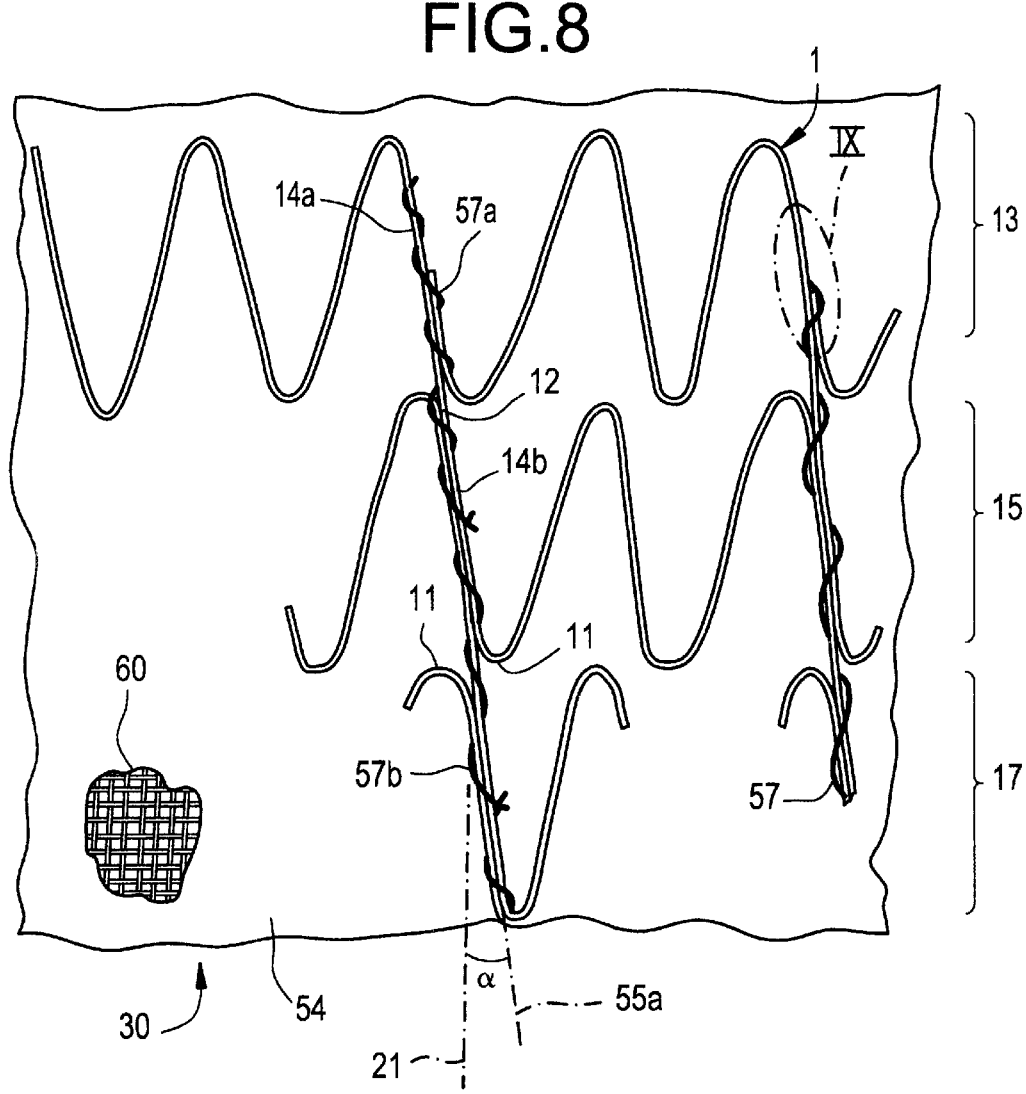
FIG. 8 is an enlarged view of the detail designated VIII in FIGS. 1 or 3, with the addition of the sleeve and the retaining threads which are characteristic of the invention.

FIG. 8 is a more detailed view of the embodiment of FIG. 7. Each flexible thread 57a surrounds and extends along one intermediate segment, e.g., 14a, and then passes to a second intermediate segment, e.g., 14b, which it is coiled around and extends along. In this manner, the thread 57 extends along the entire length of the line 55a, which has a substantially rectilinear (or slightly helical) direction and which forms an angle with respect to the axis 21 of the prosthesis that is less than approximately 40° and, more preferably, is between approximately 3° and 25°.

Figure 9:
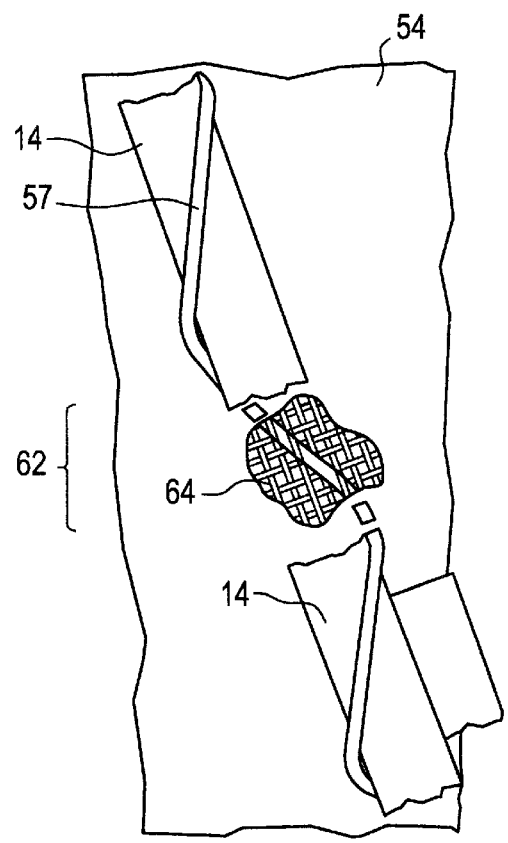
FIG. 9 is an enlarged view of the detail IX in FIG. 8.

The cut-away zone 60 illustrates the mesh structure of the flexible sleeve 54. As illustrated in FIG. 9, as the thread 57 winds along a segment of the frame 1, it extends into and interlaces with the interstices 64 of the flexible sleeve 54 before passing out of the sleeve and wrapping around the structural segment 14 once again. Thus, at each winding level or stage of the frame of the prosthesis, each of the lines 55 formed by the double length connection segments 12—each of which is connected to a single length segment 14 forming part of the zigzag undulations—is surrounded by or overwrapped by several coils of a length of flexible thread 57, which preferably passes through and extends into the internal passage of the sleeve with each coil or wrap around the segments 12, 14.

It should be noted that each thread 57 is spirally wound along the segments so as to form essentially a "straight stitch," the axes of which are substantially rectilinear. Furthermore, the thread 57 does not overlap itself or another such thread 57, nor does it reverse direction when passing from one winding level to the following one. In other words, the thread 57 passes, for example, from winding level 13 to winding level 15 to winding level 17, without returning to winding levels 13 and 15. In general, several separate threads may be used, with one thread following another, as in threads 57a and 57b, with the ends of each thread being bound about the frame 1.

By having each flexible thread 57 (or 57a, 57b, etc.) coil or wrap around a sufficient length along the structural segments, the thread 57 restrains the apices 11 near which or about which it wraps. The restraining action prevents excessive projection or protrusion of the apices 11 when the frame is bent or curved.

Figure 10:
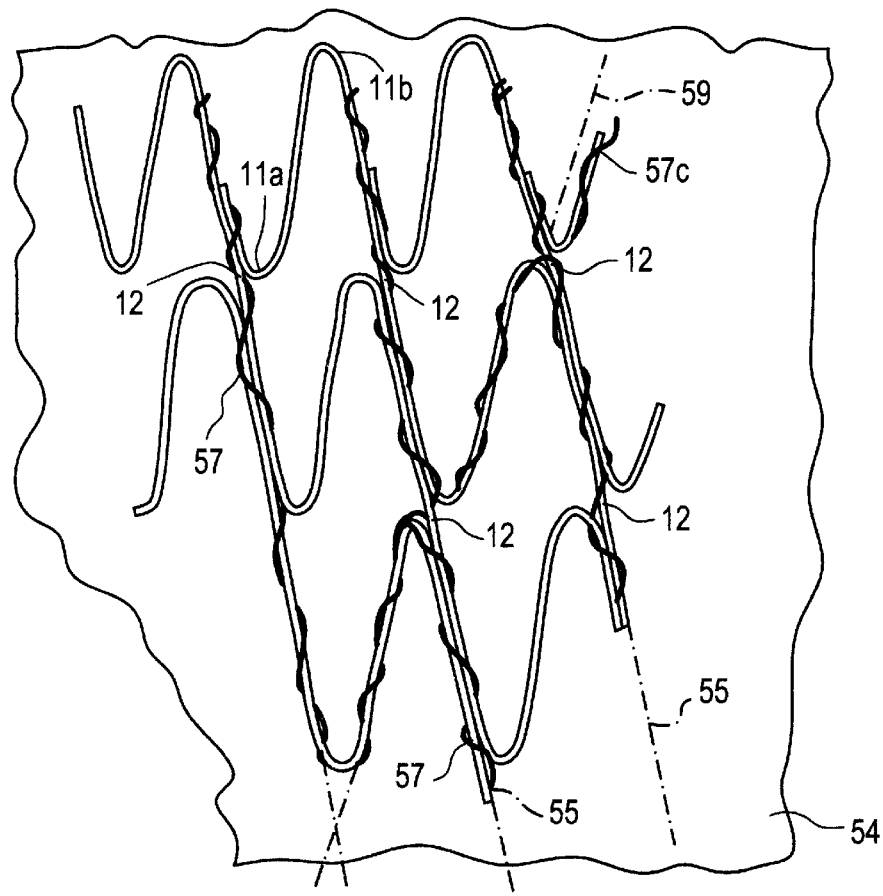
FIG. 10 is a detail view comparable to that in FIG. 8 but showing an alternative embodiment.

FIG. 10 shows another embodiment of the present invention, similar to that of FIG. 8, having a flexible sleeve 54; flexible threads 57 and 57c; segments of double length 12; and apices 11a and 11b. In addition to threads extending along lines 55, the embodiment has a supplementary flexible thread 57c, with the supplementary flexible thread 57c running along line 59 defined by the "opposing set" of elongate segments. With the supplementary thread 57c, it is possible to cross the various threads by arranging them at various places (or even systematically) not only along the lines 55, but also along all or part of the structural segments defining lines such as the line 59.

Figure 5:
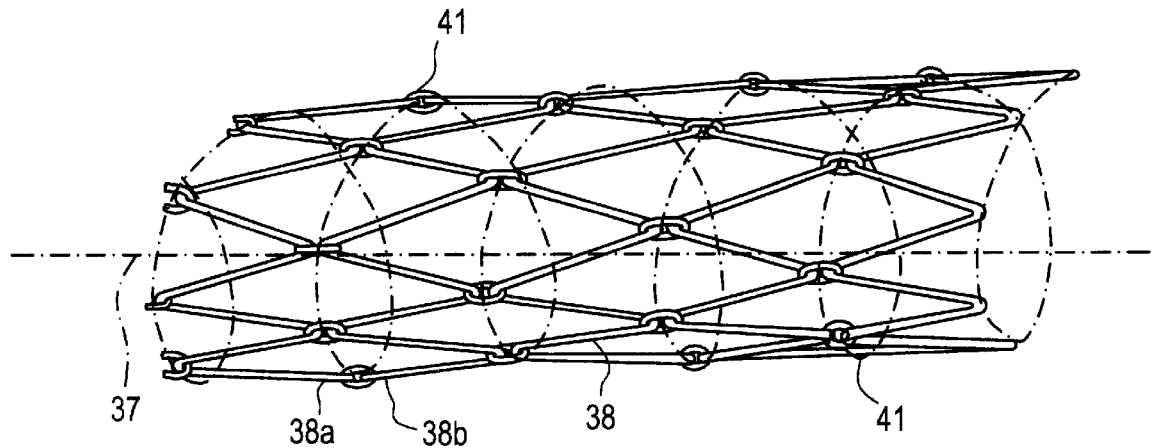
Figure 11:
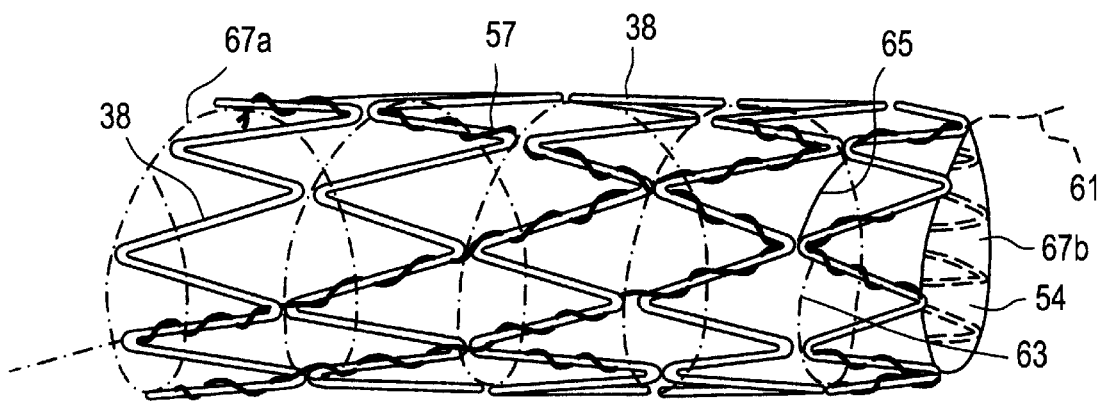
FIGS. 11 and 12 show the structures of FIGS. 5 and 6 with the addition of the flexible sleeve and the flexible retaining threads connecting the sleeve and the structures.

FIG. 11 shows a prosthesis according to the invention with the frame of FIG. 5. In this embodiment, in which the sleeve 54 is located on the inside of the frame, the structural thread is wound in a zigzagging helix, without the apices of the structure necessarily being connected to one another. The flexible threads 57 are coiled along a substantially helical direction, as in the direction 61, and may even be angularly offset at certain changes of level, such as at 63 and 65.

Figure 6:
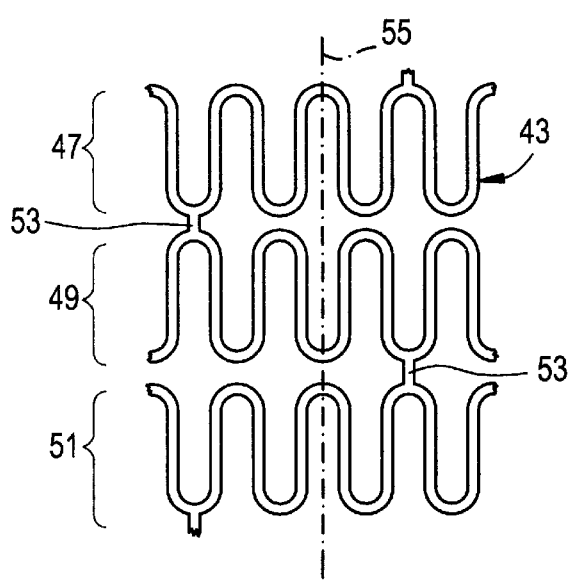
Figure 12:
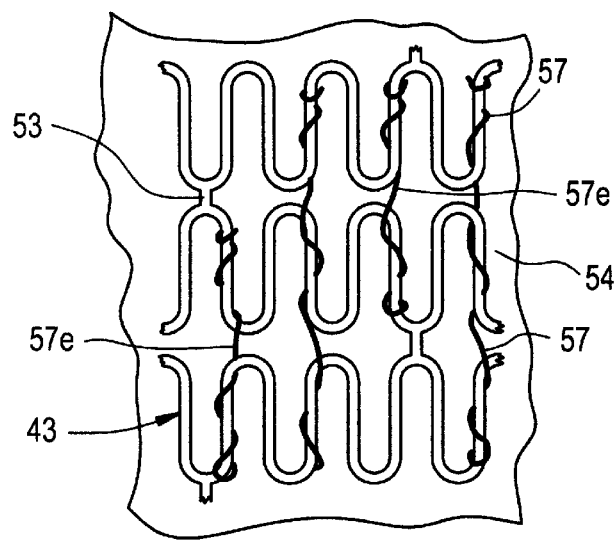

FIG. 12 shows a prosthesis having the frame shown in FIG. 6, with the addition of flexible threads 57 for securing the flexible sleeve 54 to the frame. The thread 57 wraps about a segment 43 of an undulation at a given step or level of the structure before passing to an adjacent step or level. The thread passes from stage to stage while periodically passing through the flexible sleeve 54.

In the different embodiments of the present invention, the number of stages traversed by the flexible threads 57 may vary, but each thread traverses at least two successive stages. The threads 57 preferably are bound at intervals along their length with a solid binding, e.g., they may be knotted to the frame at several points along their length. This prevents the entire thread from becoming useless if it tears at some point along its length.

Figure 1:
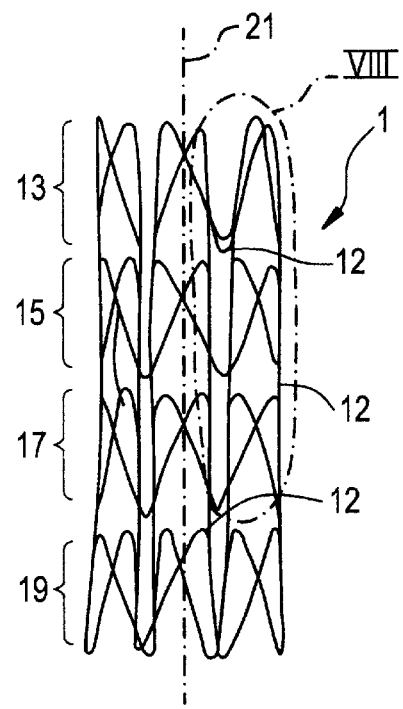
FIGS. 1–6 illustrate the frames of prior art prostheses.
Figure 2:
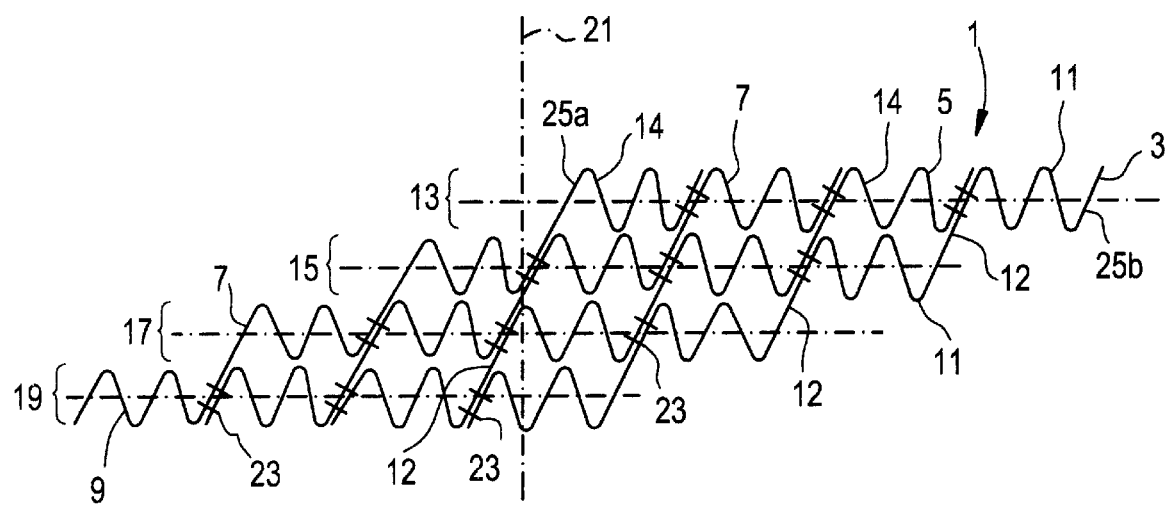
Figure 3:
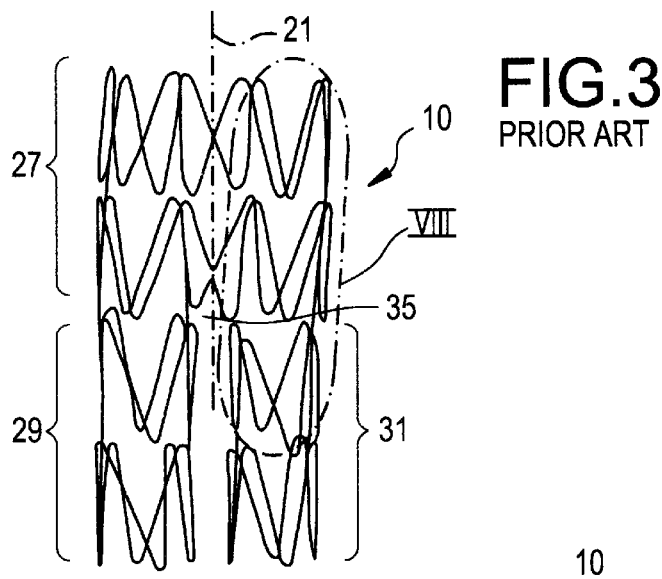
Figure 4:
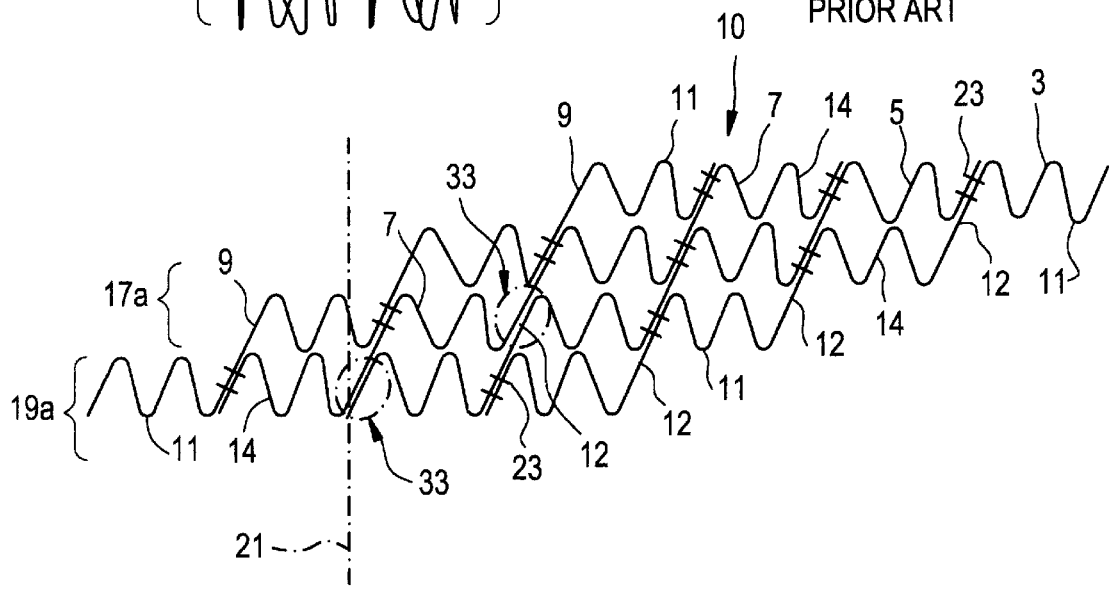

Finally, the frame or stent of the prosthesis may have several independent, axially spaced tubular sections, and may have a structure with zigzag or crenulate turns. The frame may have one or more winding levels, with the winding levels not being structurally connected to one another, so that there is no transmission of force between the winding levels. A prosthesis of this type may be obtained, for example, by severing the connection sections 12 in FIG. 2 at a given intermediate step, thus producing discontinuities and hence successive sections.

A prosthesis according to the invention has an increased capacity for curvature, the flexible sleeve 54 ensuring the cohesion between the different separate sections of the prosthesis via the flexible threads attaching the flexible sleeve to the frame 1.

While the invention has been disclosed in detail above, the invention is not intended to be limited strictly to the embodiments disclosed. It is evident that those having skill in the art may make numerous uses and modifications of and departures from the specific embodiments described herein without departing from the inventive concepts. Other embodiments are deemed to be within the scope of the following claims.

We claim:

1. A medical prosthesis adapted to be implanted into a duct of a living body, comprising:
    at least one tubular section extending along at least one axis and defining a frame, said frame comprising a plurality of adjacent, axially spaced tubular sections, each of said tubular sections comprising a meandering structure having a rigidity, the meanders of the structure having apices between which elongate segments extend;
    a flexible sleeve which is substantially coaxial with the frame to channel therein a fluid which is circulating in the duct of said body, said sleeve being made from a material; and
    attaching means for connecting the sleeve and the frame, the attaching means comprising at least one flexible thread having a rigidity which is less than that of the meandering structure, said at least one flexible thread ensuring said connection by overlapping at least one elongate segment and passing through the material of the sleeve;
    wherein said at least one flexible thread extends from one tubular section to another, adjacent tubular section so as to overlap successively along at least two elongate segments of structure of at least two of said plurality of adjacent tubular sections.

2. A medical prosthesis adapted to be implanted into a duct of a living body, comprising:
    a frame comprising a meandering structure having a rigidity, the meanders of the structure having apices between which elongate segments extend, the frame being coiled so as to form a plurality of adjacent winding levels axially spaced along at least one axis;
    a flexible sleeve which is substantially coaxial with the frame to channel therein a fluid which is circulating in the duct of said body, said sleeve being made from a material; and
    attaching means for connecting the sleeve and the frame, the attaching means comprising at least one flexible thread having a rigidity which is less than that of the meandering structure, said at least one flexible thread ensuring said connection by overlapping at least one segment and passing through the material of the sleeve;
    wherein said at least one flexible thread extends from one winding level to another, adjacent winding level so as to overlap successively along at least two segments of structure of at least two of said plurality of adjacent winding levels.

3. The prosthesis according to claim 1, wherein the at least one flexible thread passes, in the course of passing from one segment to another, close about one of the apices thereof, thereby improving retention of said apices when the prosthesis is curved in the region of said one of said apices.

4. The prosthesis according to claim 1, wherein the at least one flexible thread is wound substantially helically to form a substantially straight stitch about said at least two segments of adjacent tubular sections.

5. The prosthesis according to claim 1, wherein:
    said at least two segments of adjacent sections are situated so as to be continuations of one another along one of a substantially rectilinear and a helical direction,
    and the at least one flexible thread extends essentially along said direction.

6. The prosthesis according claim 1, wherein said prosthesis comprises several flexible threads which extend along several directions which are substantially parallel to one another.

7. The prosthesis according to claim 1, wherein:
    said prosthesis has opposite axial free ends and a length therebetween; and
    said at least one flexible thread extends over at least the majority of the length of the prosthesis.

8. The prosthesis according to claim 1, wherein the at least one flexible thread has a length and has at least one knot along its length.

9. A medical prosthesis adapted to be implanted into a duct of a living body, comprising:
    at least one tubular section extending along at least one axis and defining a frame, said frame comprising a plurality of adjacent, axially spaced tubular sections, each of said tubular sections comprising a meandering structure having a rigidity, the meanders of the structure having apices between which elongate segments extend;
    a flexible sleeve which is substantially coaxial with the frame to channel therein a fluid which is circulating in the duct of said body, said sleeve being made from a material; and
    attaching means for connecting the sleeve and the frame, the attaching means comprising at least one flexible thread having a rigidity which is less than that of the meandering structure, said at least one flexible thread ensuring said connection by overlapping at least one elongate segment and passing through the material of the sleeve, wherein said at least one flexible thread extends from one tubular section to another, adjacent tubular section so as to overlap successively along at least two elongate segments of structure of at least two of said plurality of adjacent tubular sections, said at least two segments of adjacent sections are situated so as to be continuations of one another along one of a substantially rectilinear and a helical direction, and the at least one flexible thread extends essentially along said direction.

* * * * *